(12) United States Patent
Nogueira et al.

(10) Patent No.: US 9,713,714 B2
(45) Date of Patent: Jul. 25, 2017

(54) METHOD AND SYSTEM FOR ELECTRICAL STIMULATION OF A PATIENT'S COCHLEA

(71) Applicant: ADVANCED BIONICS AG, Staefa (CH)

(72) Inventors: Waldo Nogueira, Hannover (DE); Volkmar Hamacher, Hannover (DE)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 14/649,909

(22) PCT Filed: Dec. 5, 2012

(86) PCT No.: PCT/EP2012/074435
§ 371 (c)(1),
(2) Date: Jun. 4, 2015

(87) PCT Pub. No.: WO2014/086400
PCT Pub. Date: Jun. 12, 2014

(65) Prior Publication Data
US 2015/0306388 A1    Oct. 29, 2015

(51) Int. Cl.
*A61N 1/00* (2006.01)
*A61N 1/36* (2006.01)
(Continued)

(52) U.S. Cl.
CPC ..... *A61N 1/36032* (2013.01); *A61N 1/36125* (2013.01); *A61N 1/37264* (2013.01);
(Continued)

(58) Field of Classification Search
USPC .......................................... 607/57
See application file for complete search history.

(56) References Cited

U.S. PATENT DOCUMENTS

2009/0264960 A1* 10/2009 Litvak ............... A61N 1/36032
                                                                  607/57
2010/0249880 A1    9/2010 Aschbacher et al.
(Continued)

FOREIGN PATENT DOCUMENTS

WO    WO-2010/088324    8/2010
WO    WO-2010/091339    8/2010
(Continued)

OTHER PUBLICATIONS

International Search Report and Written Opinion received in International Application No. PCT/EP2012/074435, dated Aug. 29, 2013.
Cohen, Lawrence T., "Spatial spread of neural excitation in cochlear implant recipients: comparison of improved ECAP method and psychophysical forward masking," *Hearing Research*, Elsevier Science Publishers, Amersterdam, NL, vol. 179, pp. 72-87, dated Oct. 31, 2002.
(Continued)

*Primary Examiner* — Nicole F Johnson
(74) *Attorney, Agent, or Firm* — ALG Intellectual Property, LLC

(57) ABSTRACT

A system includes a cochlear implant electrode arrangement comprising a plurality of stimulation channels; means for dividing an audio signal into a plurality of analysis channels; means for establishing an electrode-nerve-interface model of hearing stimulation via the cochlear implant electrode arrangement; means for determining a signal level value and a noise level value for each analysis channel by analyzing the respective frequency domain signal; means for determining a noise reduction gain parameter for at least some of the analysis channels as a function of the signal level value and the noise level value of the respective analysis channel; means for applying noise reduction to the frequency domain signal according to the noise reduction gain parameters to generate a noise reduced frequency domain signal; and means for generating a stimulation signal for each of the stimulation channels according to the noise reduced frequency domain signal.

34 Claims, 6 Drawing Sheets

(51) Int. Cl.
*A61N 1/372* (2006.01)
*H04R 25/00* (2006.01)
*A61N 1/05* (2006.01)

(52) U.S. Cl.
CPC ......... *H04R 25/353* (2013.01); *A61N 1/0541* (2013.01); *H04R 2225/023* (2013.01); *H04R 2225/43* (2013.01); *H04R 2460/01* (2013.01)

(56) References Cited

U.S. PATENT DOCUMENTS

| | | |
|---|---|---|
| 2011/0064241 A1 | 3/2011 | Kulkarni |
| 2011/0098784 A1 | 4/2011 | Schleich et al. |

FOREIGN PATENT DOCUMENTS

| | | |
|---|---|---|
| WO | WO-2011/032021 | 3/2011 |
| WO | WO-2011/032024 | 3/2011 |
| WO | WO-2011/150292 | 12/2011 |

OTHER PUBLICATIONS

Li-Ping, Y. et al., "Spectral subtraction-based speech enhancement for cochlear implant patients in background noise", *J. Acoust. Soc. Am.* 117 (2005), pp. 1001 to 1004.
Hu, Y. et al., "Use of sigmoidal-shaped function for noise attenuation in cochlear implants", *J. Acoust. Soc. Am.* 122 (2007), EL 128 to 134.
Chung, K. "Utilizing hearing aid directional microphones and noise reduction algorithms to improve speech understanding and listening preferences for cochlear implant users", *International Congress Series* 1273 (2004), pp. 89 to 92.
Litvak, L.M. et al., "Relationship between perception of spectral ripple and speech recognition in cochlear implant and vocoder listeners", *J. Acoust. Soc. Am.* 122 (2007), pp. 982 to 991.
Gustafsson, et al., "Combined Residual Echo and Noise Reduction: A Novel Psychoacoustically Motivated Algorithm", *Institute of Communication Systems and Data Processing*, RWTH Aachen, Templergraben 55, D-52056 Aachen, Germany, Sep. 8, 1998.

\* cited by examiner

METHOD AND SYSTEM FOR ELECTRICAL STIMULATION OF A PATIENT'S COCHLEA

The invention relates to a method and system for electrical stimulation of a patient's cochlea.

The sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss may be unable to derive significant benefit from conventional hearing aid systems, no matter how loud the acoustic stimulus is. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous auditory prosthesis systems (e.g., cochlear implant systems) have been developed. Auditory prosthesis systems bypass the hair cells in the cochlea by presenting electrical stimulation directly to the auditory nerve fibers. Direct stimulation of the auditory nerve fibers leads to the perception of sound in the brain and at least partial restoration of hearing function.

To facilitate direct stimulation of the auditory nerve fibers, a lead having an array of electrodes disposed thereon may be implanted in the cochlea of a patient. The electrodes form a number of stimulation channels through which electrical stimulation pulses may be applied directly to auditory nerves within the cochlea. An audio signal may then be presented to the patient by translating the audio signal into a number of electrical stimulation pulses and applying the stimulation pulses directly to the auditory nerve within the cochlea via one or more of the electrodes.

Typically, the audio signal, which usually is captured by a microphone, is divided into a plurality of analysis channels, each containing a frequency domain signal representative of a distinct frequency portion of the audio signal, wherein the frequency domain signal in each analysis channel may undergo signal processing, such as by applying channel-specific gain to the signals. The processed frequency domain signals are used for generating certain stimulation parameters according to which the stimulation signals in each stimulation channel is generated. The analysis channels are linked to the stimulation channels via channel mapping. The number of stimulation channels may correspond to the number of analysis channels, or there may be more stimulation channels than analysis channels, or there may be more analysis channels than stimulation channels. Various stimulation strategies are used, such as current steering stimulation (in order to stimulate a stimulation site located in between areas associated with two or more electrodes) and N-of-M stimulation (wherein stimulation current is only applied to N of M total stimulation channels during a particular stimulation frame).

Often auditory prosthesis patients report difficulties in speech understanding in noisy environments. For example, ambient noise within a particular listening environment may adversely affect a listening experience for an auditory prosthesis patient by diminishing the ability of the patient to perceive audio signals of interest. Several attempts to attenuate noise, while keeping the speech level by specific signal processing are known.

One noise reduction approach is to estimate a signal-to-noise ratio in each analysis channel and to relatively attenuate noise-only channels, while keeping the gain in channels with high signal-to-noise ratio (SNR) relatively high. A cochlear implant (CI) system utilizing such kind of noise reduction is described in WO 2011/032021 A1. A similar system is described in WO 2011/032024 A1, wherein for determining the gain in a certain channel not only the SNR of the respective channel is taken into account but also an overall noise value obtained from the SNRs in the other analysis channels.

It has been shown empirically that such noise reduction, while being of only limited value to hearing aid users, is helpful to CI users whose ability to separate frequency information can be quite poor, see B. A. Henry et al., "Spectral peak resolution and speech recognition in quiet: Normal hearing, hearing impaired, and cochlear implant listeners", J. Acoust. Soc. Am. 118, 2005, pages 1111 to 1121; Y. Hu et al., "Use of sigmoidal-shaped function for noise attenuation in cochlear implants", J. Acoust. Soc. Am. 122 (2007), EL 128 to 134; L. M. Litvak et al., "Relationship between perception of spectral ripple and speech recognition in cochlear implant and vocoder listeners", J. Acoust. Soc. Am. 122 (2007), pages 982 to 991. In K. Chung, "Utilizing hearing aid directional microphones and noise reduction algorithms to improve speech understanding and listening preferences for cochlear implant users", International Congress Series 1273 (2004), pages 89 to 92, objective and subjective benefit of hearing-aid-type signal processing using noise reduction and beamforming for cochlear implant users is reported. In Y. Li-Ping et al., "Spectral subtraction-based speech enhancement for cochlear implant patients in background noise", J. Acoust. Soc. Am. 117 (2005), pages 1001 to 1004, benefit of noise reduction for cochlear implant users in steady-state noise, but not in babble noise, is reported. An overview on single-microphone noise estimation is found in P. C. Loizou, "Speech Enhancement: Theory and Practice", CRC Press, Boca Raton, USA, 2007.

WO 2010/088324 A1 relates to a CI system wherein a lateral suppression network is used to perform channel-specific dynamic amplitude mapping, and wherein the automatic gain control (AGC) of each channel takes into account not only the signal level in the respective channel but also signal levels from other channels, in particular from adjacent channels.

US 2011/0098784 A1 relates to a CI system wherein channel-specific loudness mapping is performed according to equal loudness contours, with the stimulation signals being weighted according to independent channel-specific loudness functions.

WO 2010/091339 A1 relates to a noise reduction method for an electroacoustic hearing aid, wherein the gain in each frequency channel is reduced according to the SNR in the respective sub-band, with psychoacoustic masking of noise by speech or speech by noise being taken into account.

US 2010/0249880 A1 relates to a CI system, wherein a threshold calculation module is used to determine a sampling threshold value for each channel based on the envelope signal of the respective channel and the envelope signals of the directly neighboring channels in order to account for a masking effect from the neighboring channels; the threshold calculation module also may take into account the SNR in the channel in such a manner that stimulation is avoided when the envelope signal of the channel has a low SNR. If the envelope signal of the channel is above the sampling threshold value, the carrier signal of the channel is processed to determine a time grid for when the envelope signal of the channel is sampled.

It is an object of the invention to provide for a method of electrical stimulation of a patient's cochlea, wherein speech understanding is enhanced. It is a further object to provide for a corresponding system.

According to the invention, these objects are achieved by a system as defined in claim 1 and a method as defined in claim 17, respectively.

The invention is beneficial in that, by taking into account the hearing perception impact of stimulation channels other than the stimulation channel(s) associated with the respective analysis channel on the stimulation channel(s) associated with the respective analysis channel via an electrode-nerve-interface model, unwanted artifacts, such as distortion effects—usually resulting from noise reduction by relatively attenuating noise-only channels with regard to little-noise channels—can be reduced or avoided. In particular, taking into account the electrode-nerve-interface model, the amount of noise reduction can be estimated which can be applied without noticeable distortion of the desired speech signal. The invention is particularly beneficial at low SNRs and at non-stationary noise.

Conventional spectral subtraction noise reduction usually tends to overestimate the subtracted noise, which may result in distortion of the desired signal. By taking into account an electrode-nerve-interface model in noise reduction, such distortion may be avoided. In particular, the present invention allows to adapt the noise reduction algorithm to the individual patient: for example, patients with a poor electrode-nerve-interface representation (long spread of excitations, long recovery times and poor electrical dynamic range) are expected to have a perception less sensitive to the distortions produced by spectral subtraction noise reduction than patients having a very good electrode-nerve-interface.

Preferably, the electrode-nerve-interface model is based on individual electrical measurements of the electrode array-nerve-interface of the individual patient. Alternatively, the electrode-nerve interface model may be based on an average of electrical measurements of electrode array-nerve-interfaces of various patients.

Preferably, the electrode-nerve-interface model is based on EFI (electrode field imaging) measurements or on SOE (spread of excitation) measurements.

According to one embodiment, the noise level value in each analysis channel is determined by taking into account not only the frequency domain signal in the respective analysis channel but, via the electrode-nerve-interface model, also noise in the stimulation channel(s) associated with the respective analysis channel resulting from stimulation of stimulation channels other than the stimulation channel(s) associated with the respective analysis channel. Thereby for each channel distortion resulting from noise generated by stimulation of a certain channel by spread on the neighboring channels according to, for example, the EFI function can be taken into account in order to reduce or eliminate such distortion (in other words, the effect of current spread on the spread of noise on neighboring channels can be taken into account). Thereby the effects of the other channels on a certain channel are considered, so that the noise estimation in each channel can be optimized in order to reduce or eliminate distortion.

According to an alternative embodiment, the electrode-nerve-interface model provides for each stimulation channel for an estimation of the signal perception masking threshold due to current spread from the other stimulation channels, wherein the noise reduction gain parameter is determined such that, for at least some of the stimulation channels, components of the stimulation signal corresponding to noise in the analysis channel(s) associated with the respective stimulation channel, have a level below the signal perception masking threshold. By determining and taking into account the respective signal perception masking threshold in each channel, it is possible to avoid complete elimination of noisy channels but rather reduce the (noise) level only to an extent that it is below the respective signal perception masking threshold; thereby distortion resulting from (often unnecessary) complete channel elimination is avoided.

Preferably, for at least some of the analysis channels, a masking parameter value is determined according to the electrode-nerve-interface model and is taken into account in said determining of the noise reduction gain parameter, with the masking parameter value being representative of the signal perception masking threshold.

Perferably, when determining said noise reduction gain parameter, a signal-to-mask ratio is determined for at least some of the analysis channels, with the signal-to-mask ratio corresponding to the ratio of the signal level value to the masking parameter value in case that the masking parameter value is larger than the noise level value and to the ratio of the signal level value to the noise level value in case that the masking parameter value is smaller than the noise level value.

Further, when determining of said noise reduction gain parameter, the noise reduction gain parameter may be determined according to a noise reduction gain function, wherein the argument of the noise reduction gain function is the signal-to-mask ratio in case that the signal-to-mask ratio is larger than the signal-to-noise ratio and wherein the argument of the noise reduction gain function is the signal-to-noise ratio in case that the signal-to-mask ratio is smaller than the signal-to-noise ratio.

The respective noise reduction gain parameter may be determined subsequently for each analysis channel according to a sequence which is determined based on an analysis of the audio signal. The sequence may be determined according to the signal level value and the noise level value of each analysis channel. The sequence may start with the analysis channel having the largest signal-to-noise ratio as determined from the signal level value and the noise level value.

The signal perception masking thresholds may be estimated by using the noise reduced frequency domain signal of the analysis channel having the largest signal-to-noise ratio as the input signal to the electrode-nerve-interface model.

Further preferred embodiments of the invention are defined in the dependent claims.

Hereinafter, examples of the invention will be illustrated by reference to the attached drawings, wherein.

Figure 1:
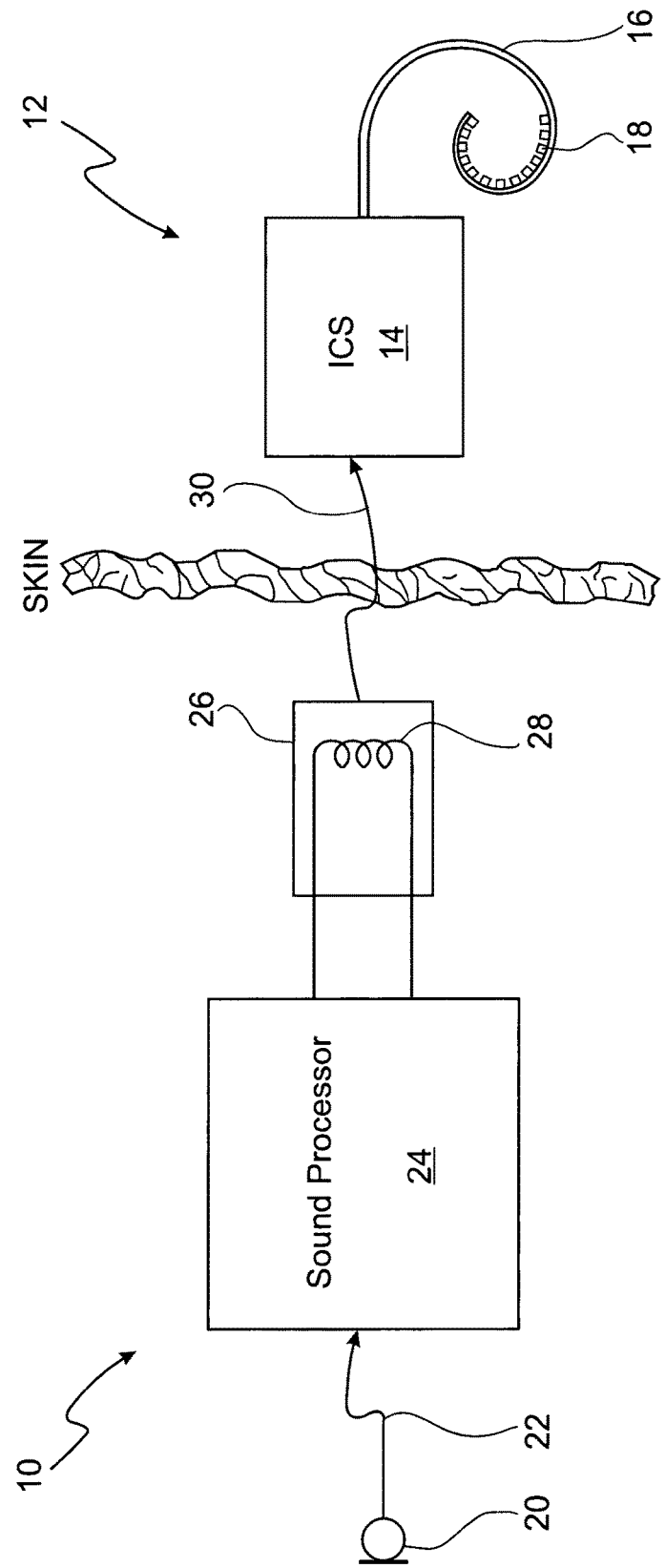
FIG. 1 is a schematic view of an example of a cochlear implant system according to the invention.

In FIG. 1 an example of a cochlear implant system is shown schematically. The system comprises a sound processing sub-system 10 and a stimulation sub-system 12. The sound processing sub-system 10 serves to detect or sense an audio signal and divide the audio signal into a plurality of analysis channels each containing a frequency domain signal (or simply "signal") representative of a distinct frequency portion of the audio signal. A signal level value and a noise level value are determined for each analysis channel by analyzing the respective frequency domain signal, and a noise reduction gain parameter is determined for each analysis channel as a function of the signal level value and the noise level value of the respective analysis channel. Noise reduction is applied to the frequency domain signal according to the noise reduction gain parameters to generate a noise reduced frequency domain signal. Stimulation parameters are generated based on the noise reduced frequency domain signal and are transmitted to the stimulation sub-system 12.

Stimulation sub-system 12 serves to generate and apply electrical stimulation (also referred to herein as "stimulation current" and/or "stimulation pulses") to stimulation sites at the auditory nerve within the cochlea of a patient in accordance with the stimulation parameters received from the sound processing sub-system 10. Electrical stimulation is provided to the patient via a CI electrode arrangement 18 comprising a plurality of stimulation channels, wherein various known stimulation strategies, such as current steering stimulation or N-of-M stimulation may be utilized.

As used herein, a "current steering stimulation strategy" is one in which weighted stimulation current is applied concurrently to two or more electrodes by an implantable cochlear stimulator in order to stimulate a stimulation site located in between areas associated with the two or more electrodes and thereby create a perception of a frequency in between the frequencies associated with the two or more electrodes, compensate for one or more disabled electrodes, and/or generate a target pitch that is outside a range of pitches associated with an array of electrodes.

As used herein, an "N-of-M stimulation strategy" is one in which stimulation current is only applied to N of M total stimulation channels during a particular stimulation frame, where N is less than M. An N-of-M stimulation strategy may be used to prevent irrelevant information contained within an audio signal from being presented to a CI user, achieve higher stimulation rates, minimize electrode interaction, and/or for any other reason as may serve a particular application.

The stimulation parameters may control various parameters of the electrical stimulation applied to a stimulation site including, but not limited to, frequency, pulse width, amplitude, waveform (e.g., square or sinusoidal), electrode polarity (i.e., anode-cathode assignment), location (i.e., which electrode pair or electrode group receives the stimulation current), burst pattern (e.g., burst on time and burst off time), duty cycle or burst repeat interval, spectral tilt, ramp on time, and ramp off time of the stimulation current that is applied to the stimulation site.

Figure 2:
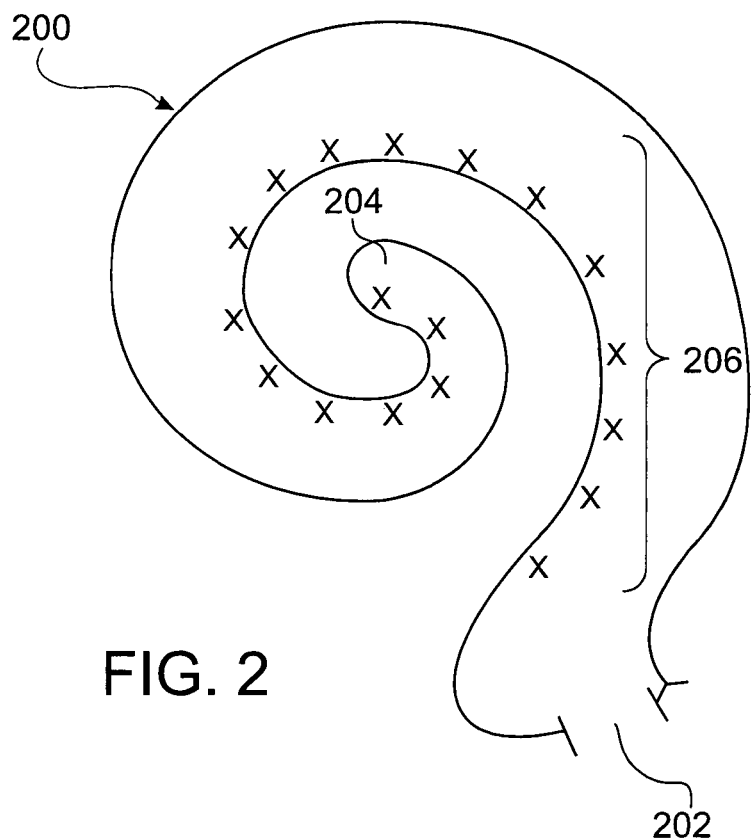
FIG. 2 is a schematic cross-sectional view of a human cochlea with marked stimulation sites.

FIG. 2 illustrates a schematic structure of the human cochlea 200. As shown in FIG. 2, the cochlea 200 is in the shape of a spiral beginning at a base 202 and ending at an apex 204.

Within the cochlea 200 resides auditory nerve tissue 206, which is denoted by Xs in FIG. 2. The auditory nerve tissue 206 is organized within the cochlea 200 in a tonotopic manner Low frequencies are encoded at the apex 204 of the cochlea 200 while high frequencies are encoded at the base 202. Hence, each location along the length of the cochlea 200 corresponds to a different perceived frequency. Stimulation subsystem 12 is configured to apply electrical stimulation to different locations within the cochlea 200 (e.g., different locations along the auditory nerve tissue 206) to provide a sensation of hearing.

Returning to FIG. 1, sound processing subsystem 10 and stimulation subsystem 12 may be configured to operate in accordance with one or more control parameters. These control parameters may be configured to specify one or more stimulation parameters, operating parameters, and/or any other parameter as may serve a particular application. Exemplary control parameters include, but are not limited to, most comfortable current levels ("M levels"), threshold current levels ("T levels"), dynamic range parameters, channel acoustic gain parameters, front and backend dynamic range parameters, current steering parameters, amplitude values, pulse rate values, pulse width values, polarity values, filter characteristics, and/or any other control parameter as may serve a particular application.

In the example shown in FIG. 1, the stimulation sub-system 12 comprises an implantable cochlear stimulator ("ICS") 14, a lead 16 and a plurality of electrodes 18 disposed on the lead 16. The lead 16 may be inserted within a duct of the cochlea in such a manner that the electrodes 18 are in communication with one or more stimulation sites within the cochlea, i.e. the electrodes 18 are adjacent to, in the general vicinity of, in close proximity to, directly next to, or directly on the respective stimulation site.

In the example shown in FIG. 1, the sound processing sub-system 10 is designed as being located external to the patient; however, in alternative examples, at least one of the components of the sub-system 10 may be implantable.

In the example shown in FIG. 1, the sound processing sub-system 10 comprises a microphone 20 which captures audio signals from ambient sound, a microphone link 22, a sound processor 24 which receives audio signals from the microphone 20 via the link 22, and a headpiece 26 having a coil 28 disposed therein. The sound processor 24 is configured to process the captured audio signals in accordance with a selected sound processing strategy to generate appropriate stimulation parameters for controlling the ICS 14 and may include, or be implemented within, a behind-the-ear (BTE) unit or a portable speech processor ("PSP"). In the example of FIG. 1 the sound processor 24 is configured to transcutaneously transmit data (in particular data representative of one or more stimulation parameters) to the ICS 14 via a wireless transcutaneous communication link 30. The headpiece 26 may be affixed to the patient's head and positioned such that the coil 28 is communicatively coupled to the corresponding coil (not shown) included within the ICS 14 in order to establish the link 30. The link 30 may include a bidirectional communication link and/or one or more dedicated unidirectional communication links.

According to an alternative embodiment, the sound processor 24 and the ICS 14 may be directly connected by wires.

Figure 3:
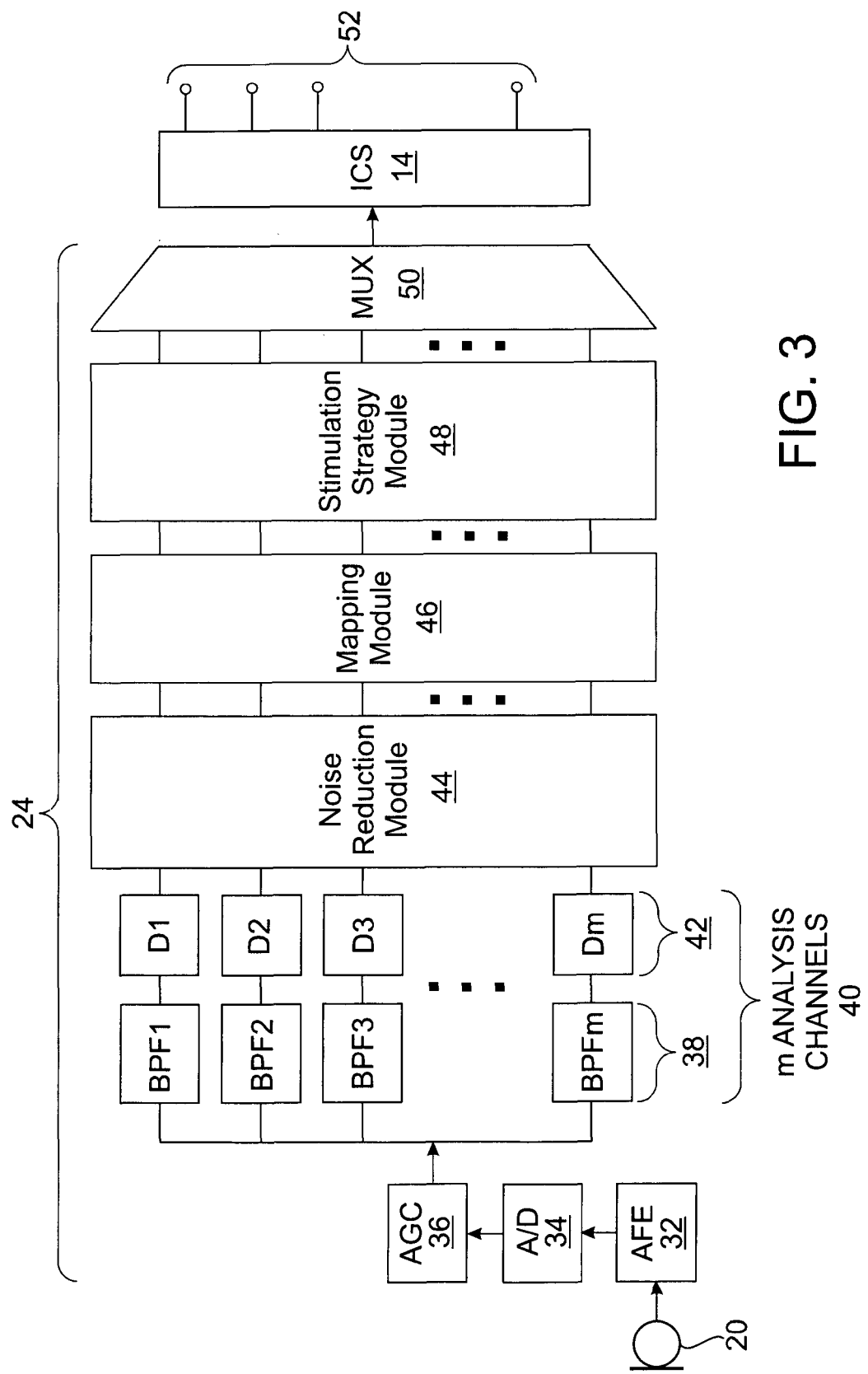
FIG. 3 is a block diagram of the signal processing structure of a cochlear implant system according to the invention.

In FIG. 3 a schematic example of a sound processor 24 is shown. The audio signals captured by the microphone 20 are amplified in an audio front end circuitry 32, with the amplified audio signal being converted to a digital signal by an analog-to-digital converter 34. The resulting digital signal is then subjected to automatic gain control using a suitable automatic gain control (AGC) unit 36.

After appropriate automatic gain control, the digital signal is subjected to a plurality of filters 38 (for example, bandpass filters) which are configured to divide the digital signal into m analysis channels 40, each containing a signal representative of a distinct frequency portion of the audio signal sensed by the microphone 20. For example, such frequency filtering may be implemented by applying a Discrete Fourier Transform to the audio signal and then divide the resulting frequency bins into the analysis channels 40.

The signals within each analysis channel 40 are input into an envelope detector 42 in order to determine the amount of energy contained within each of the signals within the analysis channels 40 and to estimate the noise within each channel. After envelope detection the signals within the analysis channels 40 are input into a noise reduction module 44, wherein the signals are treated in a manner so as to reduce noise in the signal in order to enhance, for example, the intelligibility of speech by the patient. Examples of the noise reduction module 44 will be hereinafter described by reference to FIGS. 4 and 5.

The noise reduced signals are supplied to a mapping module 46 which serves to map the signals in the analysis channels 40 to the stimulation channels. For example, signal levels of the noise reduced signals may be mapped to amplitude values used to define the electrical stimulation pulses that are applied to the patient by the ICS 14 via M stimulation channels 52. For example, each of the m stimulation channels 52 may be associated to one of the electrodes 18 or to a group of the electrodes 18.

The sound processor 24 further comprises a stimulation strategy module 48 which serves to generate one or more stimulation parameters based on the noise reduced signals and in accordance with a certain stimulation strategy (which may be selected from a plurality of stimulation strategies). For example, stimulation strategy module 48 may generate stimulation parameters which direct the ICS 14 to generate and concurrently apply weighted stimulation current via a plurality of the stimulation channels 52 in order to effectuate a current steering stimulation strategy. Additionally or alternatively the stimulation strategy module 48 may be configured to generate stimulation parameters which direct the ICS 14 to apply electrical stimulation via only a subset N of the stimulation channels 52 in order to effectuate an N-of-M stimulation strategy.

The sound processor 24 also comprises a multiplexer 50 which serves to serialize the stimulation parameters generated by the stimulation strategy module 48 so that they can be transmitted to the ICS 14 via the communication link 30, i.e. via the coil 28.

Figure 4:
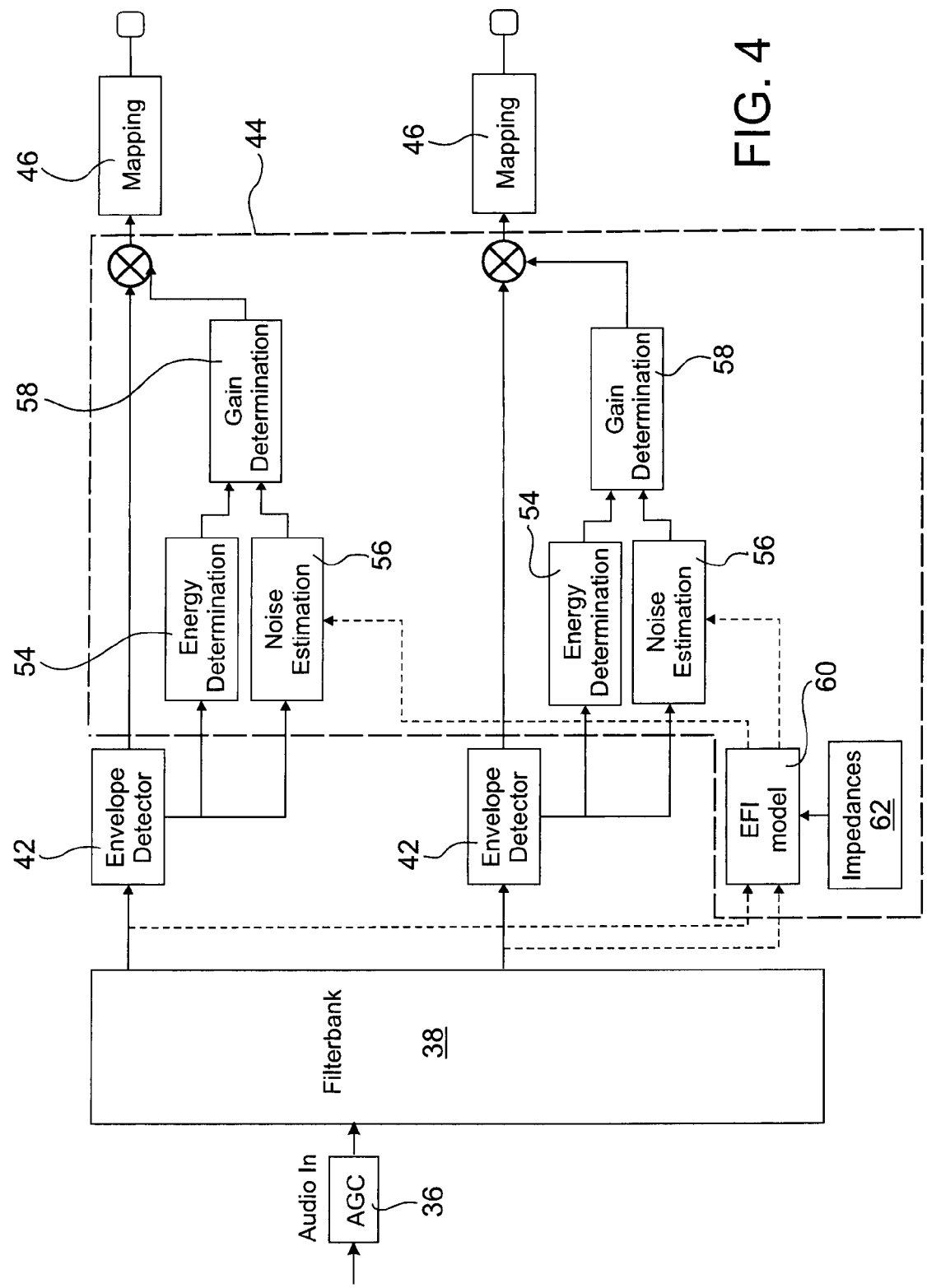
FIG. 4 is a block diagram of part of the signal processing structure of a cochlear implant system according to one example of the invention.
Figure 5:
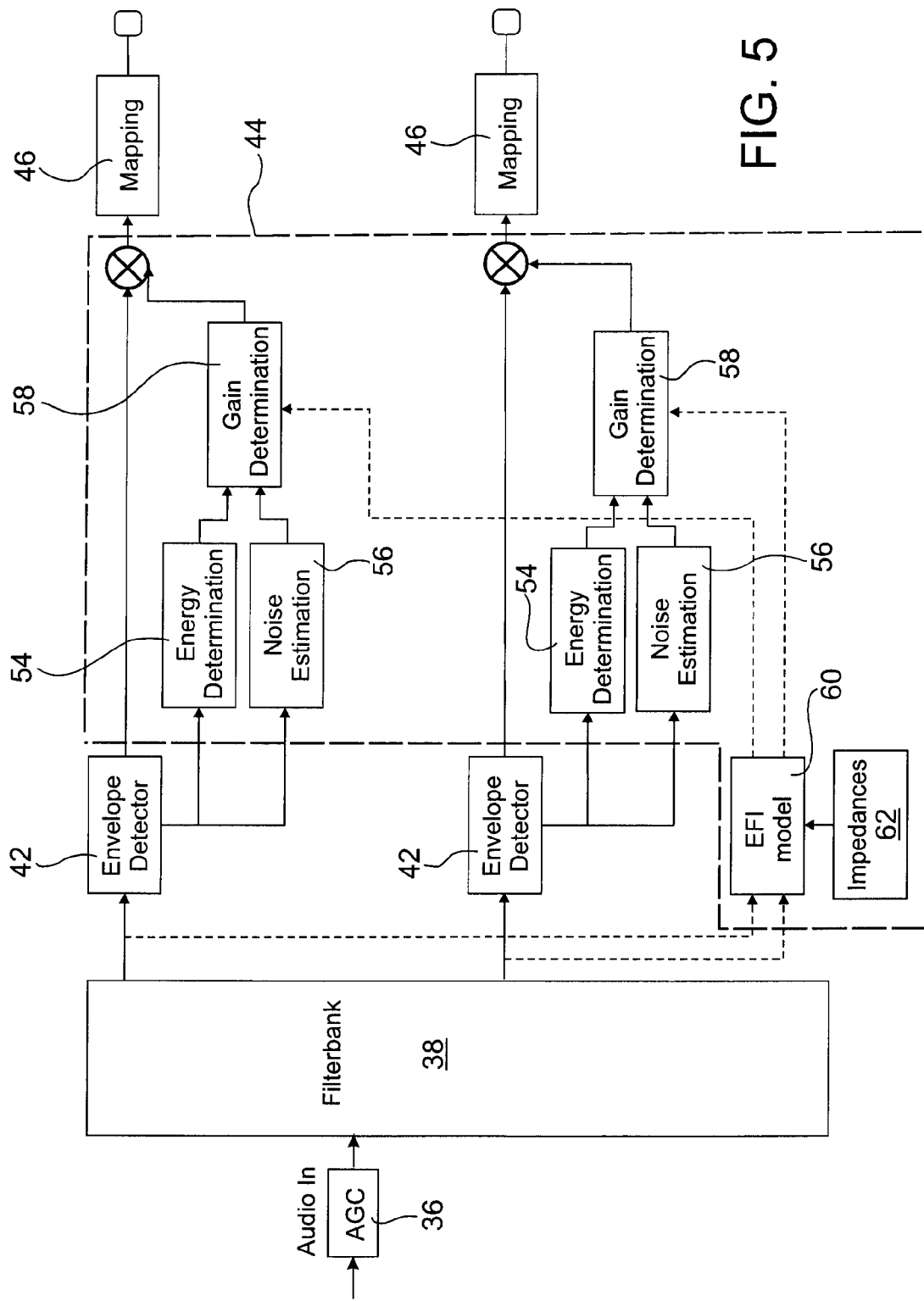
FIG. 5 is a view like FIG. 4, wherein an alternative embodiment is shown.

Two examples of the noise reduction module 44 are shown in FIGS. 4 and 5, respectively, two of the m analysis channels.

The output of the envelope detector 42 is supplied, in each analysis channel 40, to an energy determination unit 54 for determining a signal level value and to a noise estimation unit 56 for determining a noise level value. The output of the energy determination unit 54 and the output of the noise estimation unit 56 are input into a gain determination unit 58 which determines a noise reduction gain parameter from the signal level value and the noise level value for the respective one of the channels 40. For example, a SNR may be calculated from the signal level value and the noise level value for each of the in channels 40 according to:

$$SNR[M,t] = V_S[M,t] - V_N[M,t],$$

where $V_S$ and $V_N$ are the speech energy and the noise estimation energy, respectively, and M denotes the respective channel.

The desired channel-specific gain then may be computed based on a predetermined gain function F as:

$$G_{NR}[M,t] = F(SNR[M,t])$$

According to the invention, the noise reduction algorithm utilizes an electrode-nerve-interface model of hearing stimulation via the CI electrode array in order to individually optimize noise reduction, in particular to avoid or at least reduce distortion caused by noise reduction. The model describes, for each of the stimulation channels, the hearing perception impact of a stimulation signal applied to a certain stimulation channel on the other stimulation channels. The model may be based on electrical measurements of the electrode array-nerve-interface of the specific patient, or it may be based on an average of corresponding electrical measurements on various patients.

According to one example, the model may be based on EFI measurements. Such measurements are described, for example, in F. Vanpoucke et al., "The facial nerve canal: An important cochlear conduction path revealed by Clarion electrical field imaging", in Otology & Neurotology 25 (2004), pages 282 to 289. Alternatively, such model may be based on spread of excitation (SOE) measurements. Such measurements are described, for example, in L. T. Cohen et al., "Spatial spread of neural excitation in cochlear implant recipients: Comparison of improved ECAP method and psychophysical forward masking", in Hearing Research 179 (2003), pages 72 to 87.

In the examples of FIGS. 4 and 5, it is assumed that the model is based on EFI measurements, wherein the EFI model is implemented by a unit 60 which receives the measured impedances of the electrodes as an input from a memory unit 62 in order to establish an electrode-nerve-interface model of the patient. As further input, the model unit 60 is supplied with an output of the filters 38 (as shown in FIGS. 4 and 5) or with an output of the envelope detector 42 of each analysis channel 40, i.e. with a measure of the signal level/energy of each of the channels 40. Based on the measured electrode impedances and on the channel-specific signal levels, the model unit 60 determines a channel-specific output.

In the example shown in FIG. 4 the output of the model unit 60 is supplied to the noise estimation unit 56 of the respective channel, so that each noise estimation unit 56 can use the output from the model unit 60 in addition to the envelope signal of the respective channel as determined by the envelope detector 42. The output of the model unit 60 is generated in such a manner that, by using the output from the model unit 60, each noise estimation unit 56 can determine the noise level value by taking into account not only the frequency domain signal in the respective analysis channel (as determined by the envelope detector 42), but also noise in the other channels which would have an impact on the respective channel. To this end, the output of the model unit 60 provides for an estimation of the noise generated in the stimulation channel(s) associated with the respective analysis channel as a result of stimulation of the other stimulation channels. Such spread or distribution of noise on other stimulation channels is estimated by the model unit 60, so that it can be taken into account by the respective noise estimation unit 56 in order to improve the noise estimation in each analysis channel.

In conventional systems, the noise estimation in the channel M is a function depending on the temporal characteristics and amplitude characteristics of the envelope. For example, if the envelope is stationary and is below a certain threshold, the envelope may be considered to represent noise, and otherwise to represent speech. Under this condition, the noise may be updated as N[M]=N[M]+E[M] (wherein E[M] represents the envelope in the channel M).

According to the example of the invention shown in FIG. 4, noise from channels which may influence the channel M (i.e. channels which are close in space to the channel M) can be taken account, for example, by $$N[M]=N[M]+f[EFI(E[M])]$$

wherein the electrical field in the cochlea is modeled based on the measured impedances an wherein EFI represents the model of the electrode-nerve-interface.

In addition, the noise estimate may include masking effects from previous frames, i.e. temporal effects.

Figure 6:
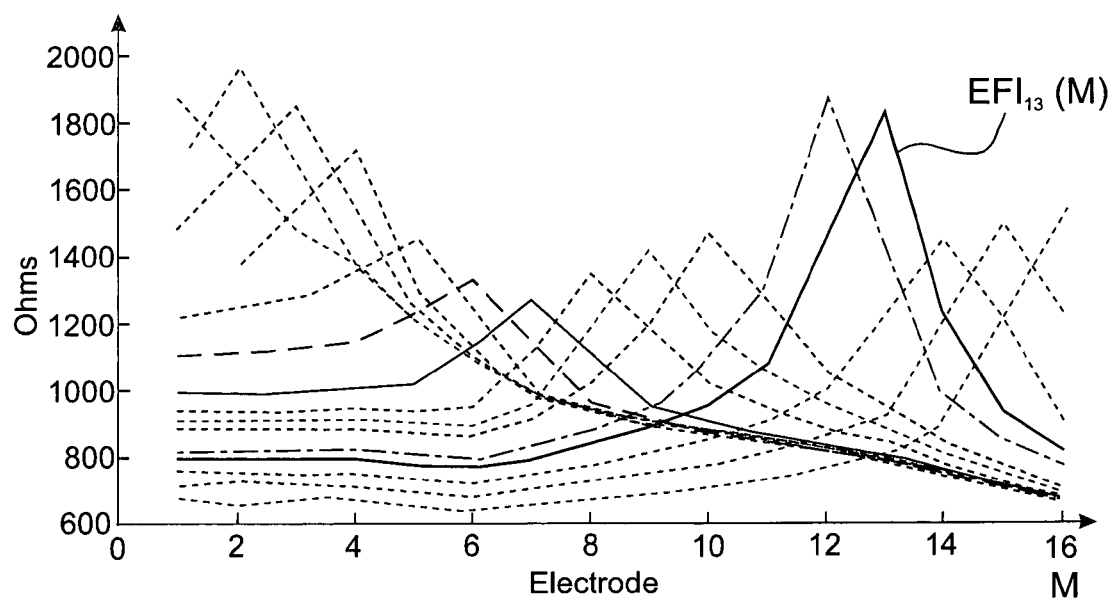
FIG. 6 is an example of an EFI model which can be used with the invention.

An example of the result of EFI measurements on an array of 16 electrodes is shown in FIG. 6, wherein for each electrode the respective impedance curve (i.e. the impedance as a function of the position within the cochlea—as exemplified by the respective electrode) is shown. Such EFI curves can be measured, for example, by using backward telemetry of the implantable stimulation subsystem 12 via the link 30.

EFI curves as shown in the example of FIG. 6 may be denoted as $EFI_i[M]$, where M denotes the channel which is measured and i denotes the channel (band) producing the "spread". It is assumed that below the level of these curves a masking effect occurs so that stimulation levels below the level of the respective curve would not result in any perception by the patient. Thus, in order to achieve a perceivable effect, the stimulation level of any electrode would have to be above the respective EFI level (for example, in the event that the electrode #13 was stimulated with a given level, the stimulation level of any of the other electrodes would have to be above the curve labeled "$EFI_{13}(M)$" (this curve indicates the potential measured at the position of the electrode M when electrode #13 is stimulated).

An alternative embodiment is shown in FIG. 5, wherein the output of the model unit 60 is not supplied to the noise estimation units 56 but rather to the gain determination unit 58 of each analysis channel 40.

The masking threshold Thr in channel M can be estimated by:

$$Thr[M,t]=E[M,t]*EFI_i[M]$$

where E[M,t] are the envelopes and the operator "*" is similar to a convolution. A signal-to-mask ratio ("SMR") can be determined as:

$$SMR[M,t]=V_S[M,t]-Mask[M,t]$$

wherein Mask[M,t] is defined as the maximum of the noise estimation and the EFI threshold in each channel, i.e.:

$$Mask[M,t]=max(E[M,t]*EFI_i[M], V_N[M,t]).$$

The channel-specific gain then is defined as $$G_{NR}[M,t]=F(SMR[M,t]), \text{ if } SMR[M,t]>SNR[M,t]$$

$$G_{NR}[M,t]=F(SNR[M,t]), \text{ otherwise}$$

Thus, the argument of the gain function of the channel M is the SNR only in case that the SMR is smaller than the SNR; in case that the SMR is larger than the SNR, the SNR is replaced by the SMR, with the SMR depending on the masking effect on the channel M caused by stimulation of the other channels, wherein the masking effect is implemented in the electrode-nerve-interface model implemented by the model unit 60.

Since in the example of FIG. 5 on the one hand the gain to be applied in a certain channel M (and hence the resulting stimulation provided by the channel), depends not only on the signal in the respective analysis channel but at least on the stimulation provided by some of the other channels (e.g. the adjacent channel M+1), and on the other hand the gain to be applied in at least some of the other channels (e.g. in channel M+1) depends on the stimulation (and hence the applied gain) in channel M, there is a mutual dependence of the gain selection in all channels (or at least in adjacent channels); for example, when the gain in the channel M is reduced due to a high noise level $V_N[M]$, the resulting reduced stimulation level in channel M is likely to have an impact on the gain selection in adjacent channel M+1. Hence it is appropriate to determine the gain to be applied, i.e. the noise reduction gain parameter, by an iterative procedure.

For example, first the channel with the largest SNR may be selected, and the noise reduction gain parameter of this channel is determined according to the SNR, without taking into account the other channels. Then the masking effect due to the EFI generated by this channel in the other channels is calculated based on the determined noise reduction gain parameter, resulting in $Thr_j[M,t]$, j=1, where j indicates the iteration of the analysis/synthesis loop. Next, the channel with the largest SMR is selected, and the noise reduction gain parameter of this channel is determined according to the SMR. Next, the channel with the largest SMR among the remaining channels is selected and the noise reduction gain parameter of this channel is determined according to the SMR of this channel. This loop is repeated until all channels have been selected.

Figure 7:
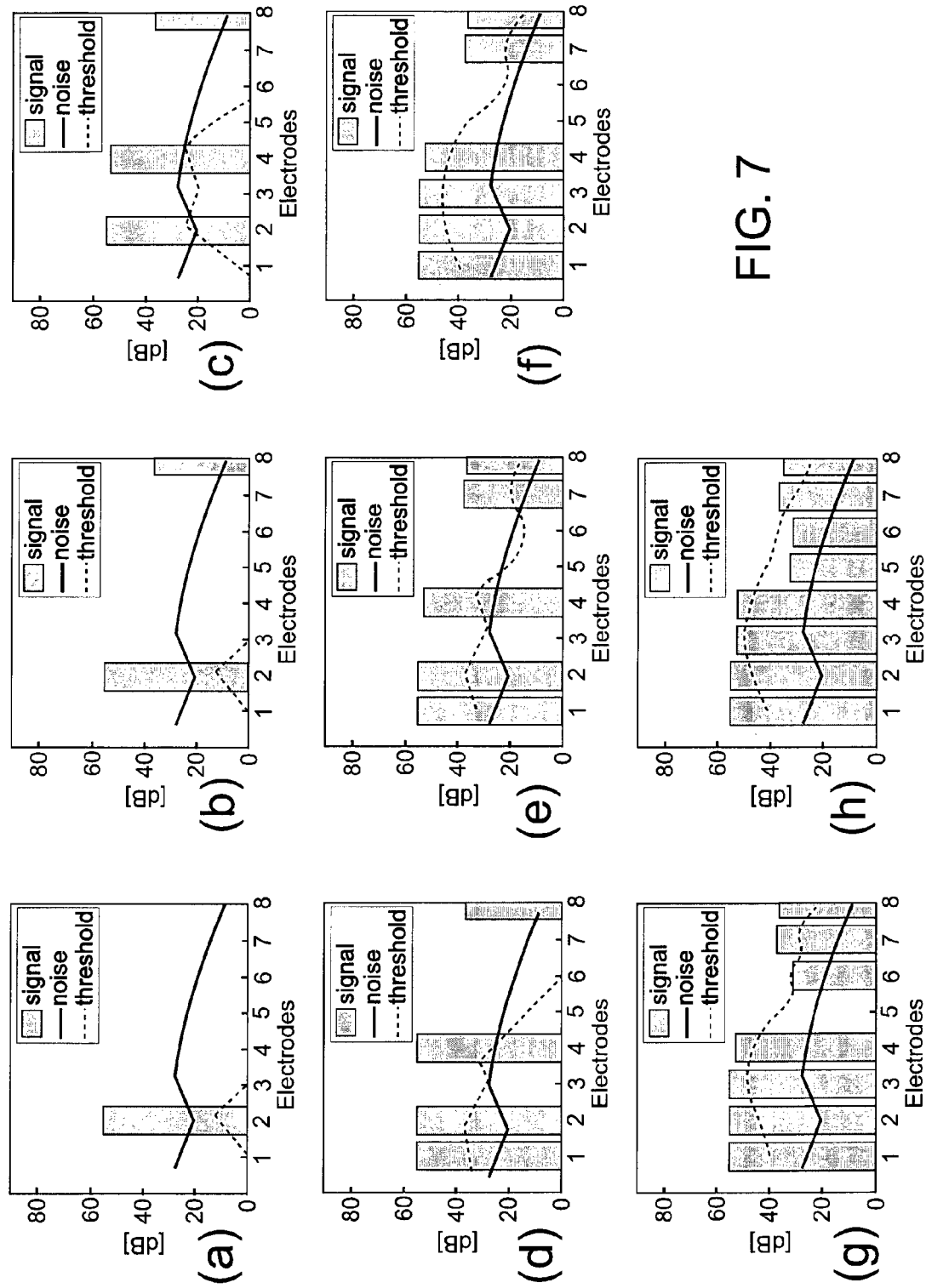
FIG. 7 is a schematic representation of the levels of the stimulation signal of the electrodes during a signal processing sequence according to the invention.

An example of this iterative procedure is shown in FIG. 7, wherein the signal energy of the stimulation signal (columns), the masking threshold (dashed lines) and the noise estimation (solid lines) are shown, with diagram (a) showing the first step and diagram (h) showing the last step (in the example it is assumed that there are 8 electrodes corresponding to 8 stimulation channels and 8 analysis channels).

For estimating the masking effect produced by a channel, the envelope of the channel is multiplied by the EFI Channels selected in the last iterations are usually less attenuated by the gain function than channels which are selected in the first iterations (the reason is that in the last iterations the masking threshold is typically higher in a certain channel than in the first iterations, so that there is usually less need to attenuate a channel selected in the last attenuations, simply because its envelope is likely to be already below the threshold).

Similar iteration procedures may be applied also in embodiments in which the output of the eletrode-nerve-interface model is used by the noise estimation unit, as in the example shown in FIG. 4, rather than by the gain determination unit.

The invention claimed is:
1. A system for electrical stimulation of a patient's cochlea, comprising
   a cochlear implant electrode arrangement comprising a plurality of stimulation channels;

means for providing an audio signal;

means for dividing the audio signal into a plurality of analysis channels, each analysis channel included in the plurality of analysis channels containing a frequency domain signal representative of a distinct frequency portion of the audio signal; and means for establishing an electrode-nerve-interface model of hearing stimulation via the cochlear implant electrode arrangement, the electrode-nerve-interface model describing, for each stimulation channel included in the plurality of stimulation channels, a hearing perception impact of a stimulation signal applied to a stimulation channel included in the plurality of stimulation channels on other stimulation channels included in the plurality of stimulation channels, wherein each stimulation channel included in the plurality of stimulation channels is associated with at least one of the plurality of analysis channels.

2. The system of claim 1, wherein the electrode-nerve-interface model is based on electrical measurements of the electrode-nerve-interface of the patient.

3. The system of claim 1, wherein the electrode-nerve-interface model is based on an average of electrical measurements of electrode-nerve-interfaces of various patients.

4. The system of claim 1, wherein the electrode-nerve-interface model is based on electrode field imaging measurements.

5. The system of claim 1, wherein the electrode-nerve-interface model is based on spread of excitation measurements.

6. The system of claim 1, further comprising:

means for determining a signal level value and a noise level value for each analysis channel included in the plurality of analysis channels by analyzing a respective frequency domain signal;

means for determining a noise reduction gain parameter for at least some of the analysis channels included in the plurality of analysis channels as a function of the signal level value and the noise level value of a respective analysis channel included in the plurality of analysis channels, wherein the hearing perception impact of stimulation of the other stimulation channels other than the stimulation channel associated with the respective analysis channel on the stimulation channel associated with the respective analysis channel is taken into account via the electrode-nerve-interface model;

means for applying noise reduction to the frequency domain signal according to the noise reduction gain parameter to generate a noise reduced frequency domain signal; and means for generating a stimulation signal for each stimulation channel included in the plurality of stimulation channels according to the noise reduced frequency domain signal and supplying the generated stimulation signals to the cochlear implant electrode arrangement in order to stimulate the patient's cochlea.

7. The system of claim 6, wherein the system is designed such that a signal-to-noise ratio is determined from the signal level value and the noise level value for each analysis channel included in the plurality of analysis channels and is used in determining the noise reduction gain parameter.

8. The system of claim 6, wherein the system is designed such that the noise level value in at least some of the analysis channels included in the plurality of analysis channels is determined by taking into account not only the frequency domain signal in the respective analysis channel but, via the electrode-nerve-interface model, also expected noise in the stimulation channel associated with the respective analysis channel resulting from stimulation of the other stimulation channels other than the stimulation channel associated with the respective analysis channel.

9. The system of claim 6, wherein the electrode-nerve-interface model provides for each stimulation channel included in the plurality of stimulation channels an estimation of a signal perception masking threshold due to stimulation of the other stimulation channels, and wherein the noise reduction gain parameter is to be determined such that, for at least some of the stimulation channels included in the plurality of stimulation channels, components of the stimulation signal corresponding to noise in an analysis channel included in the plurality of analysis channels and associated with a respective stimulation channel, have a level below the signal perception masking threshold.

10. The system of claim 9, wherein, for at least some of the analysis channels included in the plurality of analysis channels, a masking parameter value is to be determined according to the electrode-nerve-interface model and is to be taken into account in the determining of the noise reduction gain parameter, with the masking parameter value being representative of the signal perception masking threshold.

11. The system of claim 10, wherein, in the determining of the noise reduction gain parameter, a signal-to-mask ratio is to be determined for at least some of the analysis channels included in the plurality of analysis channels, with the signal-to-mask ratio corresponding to a ratio of the signal level value to the masking parameter value in case that the masking parameter value is larger than the noise level value and to a ratio of the signal level value to the noise level value in case that the masking parameter value is smaller than the noise level value.

12. The system of claim 11, wherein, in the determining of the noise reduction gain parameter, the noise reduction gain parameter is to be determined according to a noise reduction gain function, wherein an argument of the noise reduction gain function is the signal-to-mask ratio in case that the signal-to-mask ratio is larger than a signal-to-noise ratio and wherein the argument of the noise reduction gain function is the signal-to-noise ratio in case that the signal-to-mask ratio is smaller than the signal-to-noise ratio.

13. The system of claim 6, wherein a respective noise reduction gain parameter is to be determined subsequently for each analysis channel included in the plurality of analysis channels according to a sequence which is to be determined based on an analysis of the audio signal.

14. The system of claim 13, wherein the sequence is to be determined according to the signal level value and the noise level value of each analysis channel included in the plurality of analysis channels.

15. The system of claim 14, wherein the sequence starts with an analysis channel included in the plurality of analysis channels that has a largest signal-to-noise ratio as determined from the signal level value and the noise level value.

16. The system of claim 13, wherein signal perception masking thresholds are to be estimated by using the noise reduced frequency domain signal of the analysis channel having the largest signal-to-noise ratio as an input signal to the electrode-nerve-interface model.

17. The system of claim 16, wherein the sequence is to be determined based on a signal-to-mask ratio of the respective analysis channel in a decreasing order, wherein in each step of the sequence the estimation of the signal perception masking threshold is to be updated, with the noise reduced frequency domain signal of present and previous analysis channels included in the plurality of analysis channels being used as the input signal to the electrode-nerve-interface model.

18. A method of electrical stimulation of a patient's cochlea, comprising
providing an audio signal;
dividing the audio signal into a plurality of analysis channels, each analysis channel included in the plurality of analysis channels containing a frequency domain signal representative of a distinct frequency portion of the audio signal; and
establishing an electrode-nerve-interface model of hearing stimulation via a cochlear implant electrode arrangement comprising a plurality of stimulation channels, the electrode-nerve-interface model describing, for each stimulation channel included in the plurality of stimulation channels, a hearing perception impact of a stimulation signal applied to a stimulation channel included in the plurality of stimulation channels on the other stimulation channels included in the plurality of stimulation channels, wherein each stimulation channel included in the plurality of stimulation channels is associated with at least one of the plurality of analysis channels.

19. The method of claim 18, wherein the electrode-nerve-interface model is based on electrical measurements of the electrode-nerve-interface of the patient.

20. The method of claim 18, wherein the electrode-nerve-interface model is based on an average of electrical measurements of electrode-nerve-interfaces of various patients.

21. The method of claim 18, wherein the electrode-nerve-interface model is based on electrode field imaging measurements.

22. The method of claim 18, wherein the electrode-nerve-interface model is based on spread of excitation measurements.

23. The method of claim 17, further comprising:
determining a signal level value and a noise level value for each analysis channel included in the plurality of analysis channels by analyzing a respective frequency domain signal, and determining a noise reduction gain parameter for each analysis channel included in the plurality of analysis channels as a function of the signal level value and the noise level value of a respective analysis channel, wherein at least for some of the analysis channels included in the plurality of analysis channels the hearing perception impact of the other stimulation channels other than the stimulation channel associated with the respective analysis channel on the stimulation channel associated with the respective analysis channel is taken into account via the electrode-nerve-interface model;
applying noise reduction to the frequency domain signal according to the noise reduction gain parameters to generate a noise reduced frequency domain signal;
generating a stimulation signal for each stimulation channel included in the plurality of stimulation channels according to the noise reduced frequency domain signal; and
supplying the generated stimulation signals to the cochlear implant electrode arrangement in order to stimulate the patient's cochlea.

24. The method of claim 23, wherein a signal-to-noise ratio is determined from the signal level value and the noise level value for each analysis channel included in the plurality of analysis channels and is used in determining the noise reduction gain parameter.

25. The method of claim 23, wherein the noise level value in at least some of the analysis channels included in the plurality of analysis channels is determined by taking into account not only the frequency domain signal in the respective analysis channel but, via the electrode-nerve-interface model, also expected noise in the stimulation channel associated with the respective analysis channel resulting from stimulation of the other stimulation channels other than the stimulation channel associated with the respective analysis channel.

26. The method of claim 23, wherein the electrode-nerve-interface model provides for each stimulation channel included in the plurality of stimulation channels an estimation of a signal perception masking threshold due to stimulation of the other stimulation channels, and wherein the noise reduction gain parameter is determined such that, for at least some of the stimulation channels included in the plurality of stimulation channels, components of the stimulation signal corresponding to noise in an analysis channel included in the plurality of analysis channels and associated with a respective stimulation channel, have a level below the signal perception masking threshold.

27. The method of claim 26, wherein, for at least some of the analysis channels included in the plurality of analysis channels, a masking parameter value is determined according to the electrode-nerve-interface model and is taken into account in the determining of the noise reduction gain parameter, with the masking parameter value being representative of the signal perception masking threshold.

28. The method of claim 27, wherein, in the determining of the noise reduction gain parameter, a signal-to-mask ratio is determined for at least some of the analysis channels included in the plurality of analysis channels, with the signal-to-mask ratio corresponding to a ratio of the signal level value to the masking parameter value in case that the masking parameter value is larger than the noise level value and to a ratio of the signal level value to the noise level value in case that the masking parameter value is smaller than the noise level value.

29. The method of claim 28, wherein, in the determining of the noise reduction gain parameter, the noise reduction gain parameter is determined according to a noise reduction gain function, wherein an argument of the noise reduction gain function is the signal-to-mask ratio in case that the signal-to-mask ratio is larger than a signal-to-noise ratio and wherein the argument of the noise reduction gain function is the signal-to-noise ratio in case that the signal-to-mask ratio is smaller than the signal-to-noise ratio.

30. The method of claim 23, wherein a respective noise reduction gain parameter is determined subsequently for each analysis channel included in the plurality of analysis channels according to a sequence which is determined based on an analysis of the audio signal.

31. The method of claim 30, wherein the sequence is determined according to the signal level value and the noise level value of each analysis channel included in the plurality of analysis channels.

32. The method of claim 31, wherein the sequence starts with an analysis channel included in the plurality of analysis channels that has a largest signal-to-noise ratio as determined from the signal level value and the noise level value.

33. The method of claim 30, wherein signal perception masking thresholds are estimated by using the noise reduced frequency domain signal of the analysis channel having the largest signal-to-noise ratio as an input signal to the electrode-nerve-interface model.

34. The method of claim 33, wherein the sequence is determined based on a signal-to-mask ratio of the respective analysis channel in a decreasing order, wherein in each step of the sequence the estimation of the signal perception masking threshold is updated, with the noise reduced frequency domain signal of present and previous analysis channels included in the plurality of analysis channels being used as the input signal to the electrode-nerve-interface model.

* * * * *